United States Patent [19]

Kühne

[11] Patent Number: 4,507,285

[45] Date of Patent: Mar. 26, 1985

[54] STABILIZED ACTIVATED OXYGEN AND PHARMACEUTICAL COMPOSITIONS CONTAINING SAID STABILIZED ACTIVATED OXYGEN

[76] Inventor: Friedrich-Wilhelm Kühne, Paulinenstrasse 56, D-7107 Neckarsulm, Fed. Rep. of Germany

[21] Appl. No.: 482,846

[22] Filed: Apr. 7, 1983

[30] Foreign Application Priority Data

Apr. 10, 1982 [DE] Fed. Rep. of Germany ....... 3213389

[51] Int. Cl.$^3$ .............................................. A61K 33/40
[52] U.S. Cl. .................................... 424/130; 423/579; 424/149
[58] Field of Search ....................... 424/127, 130, 149; 423/579

[56] References Cited

U.S. PATENT DOCUMENTS

| 4,073,873 | 2/1978 | Caldwell et al. | 423/579 |
| 4,296,103 | 10/1981 | Laso | 424/130 |
| 4,297,333 | 10/1981 | Crawford et al. | 423/241 |
| 4,343,715 | 8/1982 | Bonaventura et al. | 252/186 |

Primary Examiner—Leonard Schenkman

[57] ABSTRACT

The invention provides a stabilized activated oxygen in matrix of chlorite ions and pharmaceutical compositions containing this stabilized activated oxygen. The stabilized activated oxygen is present in the form of a solution. The medication can be used for the treatment of skin diseases or wound healing disorders.

4 Claims, No Drawings

STABILIZED ACTIVATED OXYGEN AND PHARMACEUTICAL COMPOSITIONS CONTAINING SAID STABILIZED ACTIVATED OXYGEN

This invention relates to stabilized activated oxygen which is encorporated in a matrix of chlorite ions, and pharmaceutical compositions containing this stabilized activated oxygen.

Oxygen, as is known, is the prerequisite for the formation of chemical energy in the living cell, for example, in the formation of adenosine triphosphate. Oxygen deficiency leads to various deficiency diseases and complaints during advance age. Moreover, oxygen shortage in the tissue areas involved also leads to a severe drop in the pH value.

Many measures for the stimulation of oxygen metabolism of the living cells in the organism are aimed at the long path of the oxygen between oxygen diffusion from the pulmonary alveoli into the pulmonary capillary blood and its metabolism on the Cristea membranes of the mitochondria in the cells.

As is known, various highly active oxygen compounds develop during phagocytosis or in case of surface contact due to stimulation of the oxidative metabolism, especially the hexose monophosphate shunt of the neutrophil granulocytes and the macrophages; these highly active oxygen compounds are important in killing germs (see Cottier, *Pathogenese, Ein Handbuch Fur die arztliche Fortbildung*, Vol. 2, pages 1289–1292, Springer Verlag, 1980).

The purpose of the invention is to provide as a product, an activated oxygen in stabilized form.

This problem is solved, according to the invention, by means of a stabilized activated oxygen enclosed in a matrix of chlorite ions.

Surprisingly, the route via the pulmonary alveoli and pulmonary capillary blood can be bypassed with the help of the stabilized activated oxygen according to the invention for the purpose of stimulating oxygen metabolism in the organism because the oxygen according to the invention participates directly in the oxygen transport and outstandingly and to a hitherto unattained degree supports the function of the hemoglobin during the transport of oxygen into the cells. It is also well tolerated physiologically.

Moreover, the stabilized activated oxygen according to the invention is in a position to normalize again a lowered pH value. As a result, all of the processes associated with the cell membrane such as the energy production of the cell, the immunological processes or enzyme reactions are influenced. The stiffening of erythrocyte membranes is eliminated and erythrocyte flexibility is restored.

The stabilized activated oxygen of the invention, which is enclosed in a matrix of chlorite ions, can be produced by reacting a chlorite, such as sodium chlorite, in an aqueous solution with a hypochlorite, such as sodium hypochlorite. The reaction takes place in a molar ratio between chlorite and hypochlorite such as 1:0.2 to 1:0.3, preferably 1:0.25. There is no change in the educts in this medium within an hour. This alkaline solution of sodium chlorite and sodium hypochlorite is titrated with "chloryl sulfuric acid" to a pH value of 6.4–6.8. In the process chlorine dioxide and a charge-transfer-complex $(Cl_2O_4)^-$ are formed. Chlorine dioxide is then expelled from this complex on addition of peroxide carbonates or peroxide borates, for example, sodium perborate or sodium percarbonate and finally sodium peroxide. This produces a matrix consisting of chlorite ions containing the activated oxygen. The borate, which may develop as byproduct is later removed by crystallization.

The above reaction sequence can be explained as follows:

$$2ClO_2^- + OCl^- + 2H^+ \rightarrow 2ClO_2 + Cl^- + H_2O \quad (1)$$

$$ClO_2 + ClO_2^- \rightarrow (Cl_2O_4)^- \quad (2).$$

Half of the chlorite used is oxidized into $ClO_2$ in a redox process in accordance with equation (1). The developing chlorine dioxide forms an intensive brown charge-transfer-complex with the second half of the nonoxidized chlorite according to equation (2).

The maximum yield is attained in 60–90 minutes. The solution is then mixed, depending on future use, with small quantities of $Na_2CO_3 \times H_2O_2$ or $NaBO_2 \times H_2O_2 \times 3H_2O$, whereby the color turns brighter toward yellow. By use of the peroxide a part of the dissolved chlorine dioxide is again reduced to chlorite together with the vigorous development of oxygen. After another 15 minutes, a small quantity of $Na_2O_2$ is added to the solution which now becomes completely discolored because the residual $ClO_2$ is reduced to $ClO_2^-$. Now, with the simultaneous formation of hydroxyl ions the formation of an activated oxygen-containing matrix of chlorite ions takes place in a very slow reaction which requires at least 4 weeks and which usually takes more than 6 weeks. This reaction cannot be accelerated. The pH value rises to 13.8. Various experiments have shown that the volume of gas above the solution affects the oxygen content. A ratio of ⅔ solution to ⅓ gas volume proved to be optimal.

Stoichiometrically, in view of the quantity of chlorine dioxide formed according to equation (1), a ratio of 4:1 for chlorite to oxygen should be expected. In addition there is the possibility of oxygen formation, due to the disproportionation of hydrogen peroxide. Quantitative oxygen determinations, however, have shown that such high oxygen concentrations are not possible and that excess oxygen escapes because, on the one hand, the solubility of oxygen in $ClO_2^-$ matrix is limited and, on the other hand, an arbitrarily high partial oxygen pressure cannot be maintained and is not desired anyway because otherwise a desired peroxide reduction would be blocked.

The presence of $ClO_2^+$ ions, which are in equilibrium with $ClO_3^-$, $$OClO_2 + 2HOSO_3H \rightleftharpoons ClO_2^+ + 2SO_4H^- + H_2O \quad (3)$$

will trigger a seeding effect that directs the reaction toward chlorine dioxide:

$$ClO_2^+ + ClO_2^- \rightarrow 2ClO_2 \quad (4)$$

This counteracts the possible formation of chlorate.

Optimization experiments yielded a stoichiometric ratio of $NaClO_2:NaOCl = 1:0.21$. While here, the maximum anticipated yield of $ClO_2^-$ has not yet been completely attained, the $ClO_3^-$ content is still very small. Increasing $OCl^-$ concentrations of course do yield more $ClO_2$, this is accomplished at the expense of increased chlorate formation. The development of the charge-transfer-complex to be expected here $[Cl_2O_4]^-$ is indicated by the Raman spectrum especially by the two bands at 947 and 802 cm$^{-1}$. Their intensities should amount to about 1:1 (optimum), and deviations therefrom should be no more than 25%. The presence of undesired chlorate is evidenced by a band at 937 cm$^{-1}$. (There are also bands at 487 and 618 cm$^{-1}$).

The standard potentials for the acid medium are 1.5 volts and for the alkaline medium 0.85 volts. An excessively high hydrogen ion or hypochlorite concentration would favor the formation of chlorate (oxidation of $ClO_2^-$ to $ClO_3^-$) due to the increased oxidizing effect. The redox process, however, should be directed toward chlorine dioxide: The standard potentials $e_o$ for gaseous $ClO_2$ are 1.15 volts and for $ClO_2$ dissolved in water (present) in the form of $Cl_2O_4^-$ 0.95 volts. At a pH value of 6.4–6.8 the $e_o$ value, in other words, the standard potential for the $OCl^-/Cl^-$ system, is between 0.85 and 1.5 volts or barely sufficient to oxidize $ClO_2^-$ to $ClO_2$ and to suppress the formation of chlorate.

The resulting product of the activated oxygen contained within the matrix of chlorite ions can be represented by the general formula

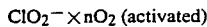
$ClO_2^- \times nO_2$ (activated)

in which n signifies the value 0.1–0.25.

The experimentally determined oxygen contents vary about 75 ppm in a 3-year-old solution. In a freshly prepared solution the initial values are over 200 ppm, and after 4 weeks they fall to the final value of 75 ppm. This value is stable over years. The results reveal surprisingly high values in a view of the fact that, normally, the solubility of oxygen declines rapidly in a solution as the salt content increases.

The activated oxygen stabilized according to the invention, which is contained in a matrix of chlorite ions, can be used in various fields, for example, in medicine and in veterinary medicine, in cosmetics, for the sterilization of food and drinking water, and as feed additives. General areas of medical application are to be found in the fields of disinfectants and chemoprophylaxis. The stabilized activated oxygen according to the invention can especially be used, for example, for the treatment of skin diseases such a herpes simples, herpes zoster, acne or burns, or wound healing disorders or for macrophage and phagocyte stimulation. In particular, an arteriopathy and an alopecia areata can be influenced significantly. With melanomes significant remissions have been obtained.

Other areas of application for the stabilized activated oxygen according to the invention are in the technical field. For example, the stabilized activated oxygen can be added to mineral oil products to attain a better energy yield when these products are burned.

EXAMPLE 1

In a closed vessel a solution of 106.4 g (1 mole) of sodium chlorite was mixed in 1 l of distilled water with 92.8 ml of a sodium hypochlorite solution containing 13% active chlorine, corresponding to 0.21 moles of sodium hypochlorite. This solution, which had a pH value of 10.4, was stirred carefully and titrated dropwise to a pH value of 6.4–6.8 with 5.3 ml of a chloryl sulfuric acid (made by adding 157.35 mg of $KClO_3$ to 122.5 ml sulfuric acid with a density of 1.6) corresponding to 6.81 mg ($55.6 \times 10^{-6}$ moles) $KClO_3$ as a catalyst. After a reaction time of 90 minutes, the solution was carefully mixed with 6 g (0.039 moles) of sodium perborate ($NaBO_2 \times H_2O_2 \times 3H_3O$), and chlorine dioxide was then expelled with vigorous stirring. After a powerful reaction, lasting 15 minutes, the reaction mixture obtained was mixed with 12 g (0.154 Moles) sodium peroxide ($Na_2O_2$). The resulting exothermal reaction was controlled by constant stirring. After about 6 weeks the product was filtered from the precipitated sodium borate in the form of an aqueous solution of a complex consisting of activated $O_2$ and $ClO_2^-$.

The solution obtained had a pH value of between 13.5 and 13.8 but did not have the character of a lye. It was a water clear liquid that could be mixed with alcohols, and had a melting point of $-3°$ C. and a conductivity of 3.45 mS.cm$^{-1}$ (activated oxygen). In the Raman spectrum it essentially showed bands at 403, 802 (chlorite) and 1562 cm$^{-1}$ (activated oxygen). To characterize the last-mentioned band, a preparation was made according to the above method using $D_2O$ because the $O_2$ band in the Raman spectrum was partly covered by the $\delta(OH_2)$ band. In the concentrate thus obtained it was possible clearly to determine the $O_2$ band at 1562 cm$^{-1}$ since $\delta(OD_2)$ appears at lower wave numbers because of the isotope effect. The O-O interval of the activated oxygen contained in the chlorite matrix was calculated at 123 pm. Thus, this bonding was considerably prolonged compared to the nonactivated oxygen (120 pm).

By means of high-pressure liquid chromatography, there was obtained a characteristic RT value for the absorption peak at 196 mm amounting to 2.14, which clearly differs from peroxide, chlorite, hypochlorite, and chlorate.

EXAMPLE 2

The operating procedure used in example 1 was repeated, but 0.049 moles of sodium percarbonate were used instead of 0.039 moles of sodium perborate. The product obtained corresponded to the product in example 1.

EXAMPLE 3

Pharmaceutical preparation

A medicinal solution was made from the product in Example 1 by diluting it with distilled water in a ratio of 1:50; that medication had a pH value of 11.45–11.6 and was physiologically tolerated.

What is claimed is:

1. Stabilized activated oxygen which is enclosed in a matrix consisting of chlorite ions as represented by the general formula

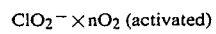
$ClO_2^- \times nO_2$ (activated)

wherein n has the value 0.1–0.25, having an $O_2$ band at 1562 cm$^{-1}$ in the Raman spectrum and an O-O interval of 123 pm, obtained by reacting a chlorite in an aqueous solution with a hypochlorite in a molar ratio between chlorite and hypochlorite of 1:0.2 to 1:0.3, titrating the obtained alkaline solution with chloryl sulfuric acid to a pH value of 6.4–6.8 to form chlorine dioxide and a charge-transfer-complex $(Cl_2O_4)^-$, expelling chlorine dioxide from this complex by addition of a peroxide selected from the group consisting of peroxide carbonates and peroxide borates, adding sodium peroxide, permitting the reaction mixture to stand for at least 4 weeks, and separating the resultant aqueous solution containing the complex of activated oxygen and chlorite ions from the carbonate or borate which precipitates from the reaction mixture.

2. Stabilized oxygen according to claim 1, present in the form of a concentrated solution with a pH of 13.5 to 13.8.

3. Stabilized oxygen according to claim 1, present in the form of a concentrated solution with a pH of 11.45 to 11.6.

4. A stabilized oxygen solution according to claim 3, which contains sodium and potassium in a ratio of 30:1.

* * * * *